United States Patent [19]

Wason

[11] 3,977,893

[45] *Aug. 31, 1976

[54] AMORPHOUS PRECIPITATED SILICEOUS PIGMENTS AND IMPROVED PROCESS FOR PRODUCING SUCH PIGMENTS

[75] Inventor: Satish K. Wason, Havre de Grace, Md.

[73] Assignee: J. M. Huber Corporation, Locust, N.J.

[ * ] Notice: The portion of the term of this patent subsequent to June 1, 1993, has been disclaimed.

[22] Filed: Aug. 20, 1975

[21] Appl. No.: 606,036

Related U.S. Application Data

[63] Continuation of Ser. No. 403,129, Oct. 3, 1973, abandoned.

[52] U.S. Cl. .......................... 106/288 B; 106/309; 423/339; 423/335
[51] Int. Cl.² .......................................... C09C 1/30
[58] Field of Search ...................... 106/288 B, 309; 423/335, 339

[56] References Cited
FOREIGN PATENTS OR APPLICATIONS
710,105    6/1954    United Kingdom................. 423/335

*Primary Examiner*—Patrick P. Garvin
*Assistant Examiner*—J. V. Howard
*Attorney, Agent, or Firm*—Robert L. Price; Harold H. Flanders

[57] ABSTRACT

A process for producing precipitated silicic acid pigments having new and improved properties is disclosed. The pigments are produced by the simultaneous introduction of a solution of an alkali metal silicate and an acid, such as sulfuric acid, into an aqueous receiving medium which contains a salt or electrolyte. The pH of the aqueous receiving medium is adjusted prior to the introduction of the acid and silicate so that it is the same or equal to that pH at which the precipitation of the pigment is effected. The electrolyte is preferably a metal salt of the acid used for acidulation of the silicate. The acid and silicate are added to the receiving medium at a rate such that the precipitating pH is maintained constant. The products of the invention are characterized by their high abrasiveness and have a relative cleaning ability or scale (RCS) equivalent to high grade phosphates used as polishing agents in toothpastes and a superior fluoride compatibility to that of said phosphates. The silicates used in the process are preferably those which are partially polymerized and have an $SiO_2/Na_2O$ ratio of at least 2.0.

5 Claims, No Drawings

3,977,893

AMORPHOUS PRECIPITATED SILICEOUS PIGMENTS AND IMPROVED PROCESS FOR PRODUCING SUCH PIGMENTS

This is a continuation of application Ser. No. 403,129, filed Oct. 3, 1973, now abandoned.

The present invention relates to silicic acid pigments and to a unique process for producing synthetic precipitated silicas having a unique combination of physical and chemical properties.

As known in the art, precipitated silicic acid pigments can be prepared by the acidulation of an aqueous silicate solution with an acid such as sulfuric acid, hydrochloric acid, etc. Examples of prior techniques which involve the acidulation of a silicate solution to produce siliceous pigments are disclosed in U.S. Pat. Nos. 3,110,606 and 3,582,379. In general it is known that the nature or characteristics of the above discussed products, sometimes herein referred to as silicas, depend on the specific reaction conditions employed, as for example, the precipitating pH, the reaction temperature, etc. Notwithstanding this fact, prior known pigments are characterized by, and have, the following properties: high structure, high wet cake moisture content, high oil absorption, low valley abrasion, high surface area and low pack density. In this regard, and due to properties such as high oil absorption, high surface area, etc., the pigments have been widely used as reinforcing pigments in rubber, in the manufacture of paper, as moisture conditioners and the like.

The high wet cake moisture content is disadvantageous however, in that the drying and filtration rates are increased, thus increasing the overall cost of the final product. For example, in the conventional production of silicic acid pigments (as defined above) the wet cake moisture content of the product (following filtration of the precipitated reaction mass) is approximately 82%. This means that there can be recovered only 18 parts of dry pigments from 100 parts of wet cake.

Further, the low abrasiveness of the known silica and silicate pigments renders them unsuitable for many uses. For example it is well known that conventional synthetic precipitated silicas are unsuitable as polishing and abrasive agents in toothpaste compositions. See German Pat. No. 974,958; French Pat. No. 1,130,627; British Pat. No. 995,351; Swiss Pat. No. 280,671 and U.S. Pat. No. 3,250,680. U.S. Pat. No. 3,538,230 specifically discloses that known amorphous silicas such as precipitated silicas, pyrogenic silicas and aerogels are unsuitable for dentifrice use because of their initial small particle size and because of the ease in which they break down into small particle sizes which result in poor cleaning ability.

In this regard, a primary function of abrasive or polishing agents in toothpaste is to remove stains, food debris and bacterial plaque from the tooth surface. Ideally the polishing agent should provide maximum cleaning action at acceptable abrasive levels and must be compatible at loadings of from about 15% up to 50% with the other toothpaste formula ingredients. Examples of known polishing agents include aluminas, thermosetting resins (as, e.g., melamine-formaldehyde resins), zirconium silicates and various phosphate salts or compounds such as beta tricalcium orthophosphate. Specific examples of phosphate polishing agents are disclosed in U.S. Pat. Nos. 3,169,096; 3,359,170 and 3,442,604.

In summary the present invention relates to the production of finely divided precipitated silicas which, because of their new and unique properties, can be used as a polishing agent in toothpaste compositions. In its broadest aspect, the invention is based on the discovery that high abrasion precipitated silicas, having superior fluoride compatibility and cleaning properties equivalent to the aforementioned phosphates, can be produced by the simultaneous introduction of an acid and an alkali metal silicate into an aqueous reaction medium which contains an electrolyte, such as sodium sulfate, and thereafter effecting the precipitation of the finely divided pigment at a constant pH. Significant process variables include the $SiO_2/Na_2O$ mole ratio of the alkali metal silicate and the initial pH of the reaction medium. With regard to the latter, the pH of the aqueous reaction medium must be adjusted prior to the introduction of the acid and silicate so that it is the same or equal to that pH at which the precipitation of the pigment is carried out. As will be discussed in more detail hereinbelow, the salt or electrolyte employed or added to the reaction medium at the outset is preferably a metal salt of the acid used for acidulation. For example, if sulfuric acid is employed, the electrolyte would comprise a metal sulfate such as sodium sulfate. Preferred electrolytes comprise sodium, lithium, potassium, and ammonium sulfate when the acid is sulfuric acid. If sodium silicate is acidulated with sulfuric acid then sodium sulfate would be the preferred electrolyte.

As indicated, the product of the invention has a unique combination of physical and chemical properties including high abrasion and a cleaning ability or action equivalent to that of known phosphate and other cleaning or polishing agents. This was truly unexpected and, in part, embodies the concept or discovery upon which the instant invention is based.

It is accordingly a general object of the present invention to provide a process for producing precipitated silicic acid pigments having a unique combination of physical and chemical properties.

Another and more particular object is to provide improved synthetic amorphous precipitated silicas which have particular utility for use as an abrasive or polishing agent for dentifrice compositions.

A further object is to provide a novel process for producing precipitated amorphous silicas which have unexpected properties as compared to conventionally known precipitated pigments, such properties including low structure, high abrasion, high pack density, and high cleaning action in toothpastes.

The manner in which the foregoing and other objects are achieved in accordance with the present invention will be better understood in view of the following detailed description which discloses particularly advantageous method and composition embodiments for illustrative purposes.

As discussed above silicic acid pigments are conventionally produced by the acidulation of an aqueous silicate solution with an acid. In other words a silicate solution is charged to a reactor with the solution then being acidulated by the introduction of an acid. More recently however (and before turning to the specific details of the invention) there has been developed, as disclosed in U.S. application Ser. No. 285,966, a process for producing siliceous pigments having improved properties wherein a salt or electrolyte is employed to prepolymerize an alkali metal silicate solution prior to its acidulation with an acid. In accordance with the teachings of this application an alkali or alkaline earth salt is first added to a solution of the alkali metal silicate, e.g., sodium silicate, with the latter being prepolymerized by the addition of the salt. The said silicate solution is then heated to a temperature in the range of from 100° to 200°F, preferably on the order of from about 150°–175°F. The acidulating agent or acid, e.g., sulfuric acid, is next charged to the reactor until the precipitation of the silicate is complete. The reaction or precipitation is carried out at a pH in the range of from about 6.5 to 11.0. At the end of the precipitation, an excess of the acid is preferably added to bring the pH of the pigment within the range of from about 5.5 to 6.5 and the reaction mass is filtered, washed and dried. In a first method embodiment disclosed by this application, the entire solution of the salt induced polymerized silicate is initially charged to reactor. In another embodiment one-half to two-thirds of the silicate is initially charged to the reactor with the remaining silicate being added with the acid.

In contrast, in accordance with the present invention an aqueous receiving medium, i.e., water, is first charged to the reactor. The electrolyte is then added to the water and the pH of the water-electrolyte media is adjusted such that it is the same at which the precipitation of the pigment is to be carried out. In the practice of the invention the precipitating pH should be in the range of 8 to 10.4. Thereafter, aqueous solutions of the acid and silicate (as to be discussed in more detail hereinbelow) are added simultaneously in a manner and at a rate such that the reaction or precipitation is carried out at the preset, constant pH. After the pigment has been completely precipitated and depending upon the ultimate or intended use of the pigment the pH can be reduced or adjusted by the addition of acid, etc. While the product of the aforesaid application Ser. No. 285,966 has high abrasiveness and can be advantageously used in dentifrice compositions, it has unexpectedly been discovered that products produced in accordance with the method of the instant invention have significantly improved cleaning ability or action, with the latter being the same as or equal to that of high grade phosphate toothpaste polishing agents. In addition and as previously noted the products, when used in toothpaste formulations, have a fluoride compatibility (i.e., the fluoride is available in its soluble form and not converted for example, to an insoluble salt, etc.) that is superior to, and not subject to the disadvantages of, known phosphates, such as calcium pyrophosphate.

As will be seen from the above and turning now to further specific details in the practice of the invention, the starting materials include an electrolyte; an alkali metal silicate and an acid. As used herein the term alkali metal silicate includes all the common forms of alkali silicates, as for example, metasilicates, disilicates and the like. Water soluble potassium silicates and sodium silicates are particularly advantageous. Because of their relatively low cost, sodium silicates are preferred. Sodium silicates are effective in any composition in which the mole ratio of the $SiO_2$ to $Na_2O$ is from about 1.0 to 4. In this regard commercially available sodium silicate solutions are more or less polymerized depending on their silica to sodium oxide ($SiO_2/Na_2O$) ratios. For example, sodium metasilicate solution (mole ratio unity) is known to be predominantly monomeric in character while water glass (mole ratio 3.3) is both monomeric and polymeric in character. As the silica to sodium oxide mole ratio of sodium silicate increases, so does the polymer to monomer ratio of its silicate anions. While sodium silicates having an $SiO_2/Na_2O$ mole ratio of from 1 to 4 may be employed, particularly advantageous results are obtained if the $SiO_2/Na_2O$ ratio is in the range of from about 2.0 to 3.3, or more preferably from about 2.0 to 2.8.

Although the commercially available silicate solutions may be more or less polymerized depending on their silica to sodium oxide ($SiO_2/Na_2O$) ratios, it has also been found that particularly advantageous and preferred results are obtained if a sulfate salt or electrolyte is added to the silicate solution prior to its simultaneous introduction with the acid into the water-electrolyte reaction or receiving medium. In other words the silicate solution itself can be pre-polymerized as per the teachings of U.S. Ser. No. 285,966. In addition, and in lieu of simply mixing the salt with the silicate solution, the silicate itself may be a product such as disclosed in U.S. application Ser. No. 193,485 wherein silica is reacted with a hydroxide in the presence of a sulfate salt to produce a polysilicate.

While the acidulating agent or acid is preferably a strong mineral acid, such as sulfuric acid, nitric acid and hydrochloric acid, it should be understood that other acids, including organic acids, as for example, acetic acid, formic, or carbonic acid, and salts of carbonic acid such as ammonium carbonate, can be employed. As noted above, the acidulating agent and silicate should preferably be added as dilute solutions thereof. Preferred results are obtained if the acidic solution is from about 10 to 25% by weight acid based on the total weight of the solution. Particularly advantageous and thus preferred results are obtained if the concentration of the silicate solution is on the order of from about 1.0 to about 2.5 pounds per gallon.

As known in the art, the term electrolyte refers to ionic or molecular substances which, when in solution, break down or disassociate to form ions or charged particles. As used herein (and referring to the electrolyte added to the water prior to the introduction of the acid and silicate solutions) the term electrolyte is intended to have its common meaning. However in the practice of the invention, and again as discussed above, the electrolyte should be compatible with the acid and silicate. Thus if sodium silicate and sulfuric acid are employed the preferred electrolyte would be sodium sulfate. If hydrochloric acid is employed as the acid (again using sodium silicate) then the electrolyte would be sodium chloride. If the silicate-acid combination is potassium silicate and sulfuric acid, then the electrolyte would be potassium sulfate, etc. Further examples of electrolytes include sodium nitrate, sodium acetate and the like. It should be noted however that the electrolyte must not be a salt that would produce a water insoluble by-product with the precipitating pigment. An example of this is calcium sulfate. Thus a calcium salt could not be used with sulfuric acid. The amount of the electrolyte used should be in the range of from 3 to 15% by weight, based on the weight of the water (receiving medium) initially added to the reaction. In general the temperature employed in precipitating the pigment of the invention is not critical and is the same as in the above discussed known processes. In a preferred embodiment the receiving medium containing the electrolyte is heated to a temperature in the range of from 100° to 200°F prior to the introduction of the silicate and acid.

As should be readily appreciated by those skilled in the art, no special equipment is required in the method herein described. In this regard, however, the reactor should be equipped with heating means, e.g., a steam jacket, in order to maintain the desired reaction temperature and should have adequate agitating means to produce a strong backflow on the body of the liquid and thus avoid zones of high concentration of the incoming reactants. It is desirable to bring the reactants together so as to produce an instantaneous reaction of all material being fed to the fullest extent reasonably possible, as such promotes uniformity of the resulting products. Storage vessels (for the reactants) connected to the reaction vessel through lines fitted with flow control means may also be provided. The reaction vessel may be equipped with an outlet line leading to a filter which may be of conventional design. After precipitation, the filtered mass is washed and dried. Such steps may also be conducted in conventional equipment, it being understood, of course, that same do not form a part of the present invention.

If the pigments of the invention are used in toothpaste compositions, the dentifrice (if in the form of a paste) may contain humectant materials and binders to give the dentifrice a smooth texture and good flowability. Glycerine, sorbitol, corn syrup, glucose and the like may be used as carriers. Examples of binders include gum tragacanth, sodium carboxymethylcellulose and the like. The above materials as well as specific formulations and ingredients of toothpaste compositions are well known in the art and are disclosed in numerous publications and patents e.g., in U.S. Pat. Nos. 2,994,642 and 3,538,230.

Before turning to specific examples, it may be noted that as used herein the term "structure" is intended to include, and is defined as, the ability of a silica material to hold water in its wet cake. When silicas, such as the aforementioned conventional precipitated silicas, hold a high percentage of water, i.e., in the neighborhood of 75 to 85%, they are known and referred to as high structure silicas. Materials holding less than 75% and preferably in the neighborhood of from about 50 to 70% water in their wet cake are referred to as low structure silicas.

The invention will be further illustrated by the following examples which set forth particularly advantageous method and composition embodiments. While the examples serve to illustrate the present invention, they are not intended to limit it thereto.

EXAMPLE 1

In this experiment dry sodium sulfate was added to 10.0 gallons of water in a 200 gallon reactor such that the sodium sulfate concentration in the reaction medium was 10%. The pH of the reaction medium was adjusted to 9.0 by the addition of sodium silicate. The reaction medium was then heated to 150°F. Sodium silicate having an $SiO_2$ to $Na_2O$ mol ratio of 2.5 and a concentration of 2.0 pounds/gallon and sulfuric acid of 11.4% concentration were then added to the reaction medium at the rate of 756 ml/min and 453 ml/minute respectively so that a constant precipitation pH of 9.0 was maintained. The sodium silicate solution employed in this Example also contained 7% sodium sulfate which was added to the solution prior to its introduction into the reactor. After 30 minutes the precipitation was complete. Excess acid was added until a slurry pH of 5.4 was reached. The reaction slurry was digested at 170°F for 20 minutes and then filtered, washed, dried and milled in the conventional manner. The product in this Example had a wet cake moisture content of 51%; a surface area of 173 $m^2/g$; a pack density of 35.6 lbs/cu.ft. and a valley abrasion (mg wire loss) of 70.2. It was further found that the product had a relative cleaning scale (RCS) of 100, which was the same as the phosphate polishing agent disclosed in U.S. Pat. No. 3,359,170, and had superior fluoride stability.

EXAMPLE 2

Example 1 was repeated except that the reaction temperature was maintained at 175°F and the precipitation pH was 10.0. Digestion temperature was 199°F. The batch was otherwise processed in the conventional manner. The properties of the product were substantially the same as in Example 1.

EXAMPLE 3

Example 1 was repeated except that the reaction temperature was maintained at 185°F and the batch was digested at 199°F. The batch was otherwise processed in the conventional manner. The properties of the product were substantially the same as in Example 1.

EXAMPLE 4

In a series of tests the general procedure of Examples 1–3 were repeated except that the precipitating pH, although held constant in each test, was varied from 8.0 to 10.4. The results were substantially the same except that it was found that the specific properties could be controlled within predetermined limits by changing the pH. In any event the products had a low wet cake moisture content, were of low structure, had relatively low oil absorptions and higher valley abrasion as compared to a control wherein conventional precipitated silica was prepared by neutralizing 1.24 lbs/gal sodium silicate (10 gal.) with 11.4% sulfuric acid. The valley abrasion of the latter was found to be 2.5 as compared to up to 167.8 (Example 3) of the products of the invention.

EXAMPLE 5

The general procedures of Example 1–4 were repeated except that nitric acid, hydrochloric acid, acetic acid and formic acid were substituted for the sulfuric acid. The results were substantially the same as in Examples 1–4. The corresponding salts (e.g., sodium nitrate, sodium chloride, etc.) were also used as the electrolyte initially charged to the reactor (in lieu of the sodium sulfate).

EXAMPLE 6

In a series of tests the general procedures of Examples 1–5 were repeated except that aqueous sodium silicates having mol ratios ($SiO_2/Na_2O$) in the range of from 1 to 3 were substituted for the 2.5 silicate of Examples 1–5. The results were generally the same as in Examples 1–5 except that it was found that the use of alkali metal silicates having an $SiO_2/Na_2O$ mol ratio within the range of from about 2.0 to 2.8 resulted in superior properties (as defined hereinabove).

EXAMPLE 7

The procedures of Examples 1–6 were repeated except that the salt employed as the electrolyte in the aqueous receiving medium was varied from 3 to 15% by weight (by increments of about 5%). The results were substantially the same as in the above Examples.

EXAMPLE 8

The procedure of Example 1 was repeated except that the sodium silicate solution did not contain any sulfate prior to its introduction into the reactor. It was found that while the valley abrasion was relatively high as compared to the control (see Example 4) the cleaning action was about 85 (RCS) as compared to 100 for the product of Example 1.

From the above Examples it is clear that the process of the invention results in silicas of lower wet cake moisture, lower structure, lower oil absorption, higher pack density and higher valley abrasion than the conventional products. In addition (and this was truly unexpected) the cleaning action of the new products when used in toothpaste were found to be very high and equal to known phosphates. The cleaning action was also approximately 50% higher than the products produced in accordance with the teachings of U.S. application Ser. No. 285,966. The valley abrasion of the latter and the products of the invention are similar.

The new process also leads to silicas of lower processing costs than regular precipitated silicas. For example, the average wet cake moisture (Examples 1 through 8) of silicas produced via the new process is approximately 53% as opposed to 82% for regular silica. This means 47 parts of dry silica from 100 parts of wet cake can be recovered. Thus, via the new process 29 parts of more dry silica or an increase of (29/18) × 100 or about 160% is obtained. The new process results in silicas of better drying and filtration rates and hence significantly lower processing costs than the precipitated silicas produced by the conventional process.

From the above it will be seen that the present invention provides a truly remarkable and simplified process for producing silicic acid pigments having new and unique properties. While preferred method and composition embodiments have been disclosed for illustrative purposes it should be understood that the invention is not limited thereto. For example, as taught in U.S. application Ser. No. 285,966, the refractive index of the precipitated pigment can be controlled by the addition of an adduct element (such as aluminum, magnesium and the like) to provide an abrasive or polishing agent for a clear translucent or transparent toothpaste composition. In this embodiment, the acid is premixed with a solution of the adduct material (e.g., aluminum sulfate) and the acid-metal salt mixture is then used for acidulating the alkali metal silicate.

As used herein, the term "pigments" is not intended to be limited to color-bearing materials which impart color to other substances or mixtures, but is intended to refer to the finely divided, powdery nature of the materials, such as silica, silicon dioxide, precipitated silica, silica abrasives, sodium alumino silicates, and the like, which are also in other contexts referred to as fillers, extenders, and reinforcing pigments.

What is claimed is:

1. A method for producing amorphous, precipitated silicic acid pigments having improved chemical and physical properties when employed in dentifrice compositions, said method comprising the steps of: providing an aqueous reaction medium containing an electrolyte, adjusting the pH of the aqueous medium to a value in the range of from about 8.0 to 10.4; simultaneously introducing an acid and a prepolymerized alkali metal silicate into said aqueous reaction medium; said acid being selected from the group consisting of sulfuric acid, nitric acid and hydrochloric acid; said prepolymerized alkali metal silicate being selected from the group consisting of sodium silicate, potassium silicate and lithium silicate, said alkali metal silicate being at least partially polymerized and having an $SiO_2/X_2O$ ratio of about 2.0 to 3.3, wherein X is selected from the group consisting of sodium, potassium and lithium, and said electrolyte comprises the sodium, potassium or lithium salt of said acid; continuing the addition of the said acid and said silicate to said aqueous reaction medium in a manner such that a substantially constant pH in the range of from about 8.0 to 10.4 is maintained and until the precipitation of said pigment is substantially complete and recovering the precipitated pigment from the aqueous reaction medium.

2. The method in accordance with claim 1 wherein said alkali metal silicate has an $SiO_2/X_2O$ mol ratio in the range of from about 2.0 to 2.8, wherein X is selected from the group consisting of sodium, potassium, and lithium.

3. The method in accordance with claim 1 wherein said electrolyte is added to the aqueous reaction medium in an amount in the range of from 3 to 15% by weight based on the weight of the reaction medium.

4. The method in accordance with claim 1 wherein the concentration of the solution of said silicate is in the range of from about 1.0 to 2.5 pounds per gallon and the acidic solution is from about 10 to 25% by weight acid based on the total weight of acidic solution.

5. The method in accordance with claim 1 wherein an adduct material selected from the group consisting of the water soluble salts of aluminum and alkaline earth metals is combined with said acid to thereby control the refractive index of the precipitated pigment and to form a metal silicate pigment having particular utility for use as an abrasion and gelling agent in clear tooth compositions.

* * * * *